(12) United States Patent
Sugiura (10) Patent No.: US 9,020,575 B2
(45) Date of Patent: Apr. 28, 2015

(54) MAGNETIC RESONANCE IMAGING APPARATUS AND MAGNETIC RESONANCE IMAGING METHOD

(75) Inventor: Satoshi Sugiura, Otawara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 998 days.

(21) Appl. No.: 11/936,281

(22) Filed: Nov. 7, 2007

(65) Prior Publication Data

US 2008/0114236 A1    May 15, 2008

(30) Foreign Application Priority Data

Nov. 10, 2006  (JP) ................... 2006-305425
Oct. 5, 2007   (JP) ................... 2007-262542

(51) Int. Cl.
*A61B 8/00*   (2006.01)
*A61B 5/055*  (2006.01)
*A61B 5/0456* (2006.01)
*A61B 17/00*  (2006.01)
*A61B 5/00*   (2006.01)

(52) U.S. Cl.
CPC ............... *A61B 5/055* (2013.01); *A61B 5/0456* (2013.01); *A61B 8/00* (2013.01); *A61B 2017/00703* (2013.01); *A61B 2017/00243* (2013.01); *A61B 5/7285* (2013.01)

(58) Field of Classification Search
CPC ...... A61B 5/7285; A61B 8/543; A61B 6/545; A61B 8/00; A61B 5/055; A61B 2017/00243; A61B 5/0456; A61B 2017/00703
USPC .................. 600/409–410, 437, 407
See application file for complete search history.

(56) References Cited

U.S. PATENT DOCUMENTS

| 4,855,910 | A  | * | 8/1989  | Bohning .................. 324/309 |
| 5,103,819 | A  | * | 4/1992  | Baker et al. ............... 607/9 |
| 5,275,621 | A  | * | 1/1994  | Mehra .................... 607/5 |
| 6,501,979 | B1 | * | 12/2002 | Manning et al. ............ 600/413 |
| 6,516,220 | B2 | * | 2/2003  | Selvester et al. ........... 600/523 |
| 7,127,092 | B2 | * | 10/2006 | Jack et al. ................ 382/128 |

(Continued)

FOREIGN PATENT DOCUMENTS

| JP | 2-88044  | 3/1990  |
| JP | 8-266502 | 10/1996 |

(Continued)

OTHER PUBLICATIONS

Igaku-Shoin Ltd., "MDCT and MRI for Cardiovascular Disease", 2005, p. 16 (abstract).

(Continued)

*Primary Examiner* — Vani Gupta
(74) *Attorney, Agent, or Firm* — Nixon & Vanderhye P.C.

(57) ABSTRACT

A apparatus includes an acquisition unit to acquire magnetic resonance data in every data group, a unit to control the acquisition unit to collect the data for one or a plurality of data groups during a collection period which is set based on a starting time phase of a cardiac cycle of the subject, a unit to determine the data among the data acquired by the acquisition unit as ineffective data if at least a part of it is related to a data group acquired during an ineffective period, and as effective data if all of it is related to a data group acquired during a period other than the ineffective period, the ineffective period being set based on an ending time point of the cardiac cycle in which the data is acquired, and a unit to reconstruct an image regarding the subject by using the effective data.

15 Claims, 5 Drawing Sheets

(56) References Cited

U.S. PATENT DOCUMENTS

| | | | |
|---|---|---|---|
| 7,454,241 B2* | 11/2008 | Beck | 600/413 |
| 7,572,231 B2* | 8/2009 | Pearlman | 600/508 |
| 2004/0097805 A1* | 5/2004 | Verard et al. | 600/428 |
| 2004/0097806 A1* | 5/2004 | Hunter et al. | 600/434 |
| 2005/0197572 A1* | 9/2005 | Williams et al. | 600/437 |

FOREIGN PATENT DOCUMENTS

| JP | 10-234695 | 9/1998 |
|---|---|---|
| JP | 2005-533 | 1/2005 |
| JP | 2005-80855 | 3/2005 |

OTHER PUBLICATIONS

Stuber et al., "Submillimeter Three-dimensional Coronary MR Angiography with Real-time Navigator Correction: Comparison of Navigator Locations", *Radiology*, vol. 212, Aug. 1999, pp. 579-587.

Plein et al., Three-Dimensional Coronary MR Angiography Performed with Subject-Specific Cardiac Acquisition Windows and Motion-Adapted Respiratory Gating, *AJR*:180, Feb. 2003, pp. 505-512.

Office Action mailed on Sep. 4, 2012 in JP 2007-262542 with English translation.

* cited by examiner

MAGNETIC RESONANCE IMAGING APPARATUS AND MAGNETIC RESONANCE IMAGING METHOD

CROSS-REFERENCE TO RELATED APPLICATIONS

This application is based upon and claims the benefit of priority from prior Japanese Patent Applications No. 2006-305425, filed Nov. 10, 2006; and No. 2007-262542, filed Oct. 5, 2007, the entire contents of both of which are incorporated herein by reference.

BACKGROUND

1. Technical Field

The present disclosure is related to a magnetic resonance imaging (MRI) apparatus for imaging a subject based on magnetic resonance data with regard to a magnetic resonance in the subject.

2. Description of the Related Art

When a heart is imaged by MRI, image quality deterioration caused by cardiac movement is desired to be suppressed. Especially, it is important that image quality deterioration due to cardiac movement is suppressed in an imaging method requiring high spatial resolution, such as coronary artery imaging or myocardial delayed enhancement. As an imaging method which suits such needs, a method to collect data selectively in a period which has less cardiac pulsation within a cardiac cycle is known by (Stuber, M. et al., "Submillimeter Three-dimensional Coronary MR Angiography with Real-Time Navigator Correction: Comparison of Navigator Locations," Radiology 1999; 212:579-587). In this method, data is collected during a period determined by a predetermined delay time and data collecting time (window time), which originates from an R-wage obtained from the subject's electrocardiographic (ECG) waveform.

Figure 5:
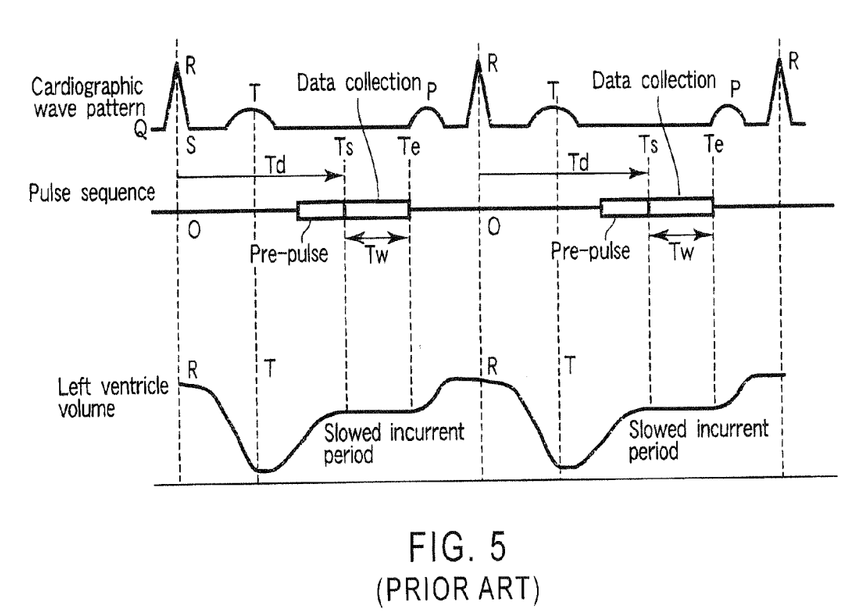
FIG. 5 illustrates an example of a pulse sequence in an MRI imaging method which collects data of a specific cardiac time phase in a cardiac cycle, such as, in coronary artery imaging or myocardial delayed enhancement.

FIG. 5 illustrates an example of a pulse sequence in an MRI method which collects data of a specific cardiac time phase in a cardiac cycle. Data is collected during a period which starts at a starting time point Ts, where the cardiac movement reduces, and ends at an ending time point Te, where the cardiac movement resumes. However, usually, the starting time point Ts is a point of time where a delay time Td has lapsed after the R-wave appears in the subject's ECG waveform. Further, the ending time point Te is a point of time where the window time Tw has lapsed from this starting time point Ts. In this manner, data is collected only in a period with less cardiac movement, which is generally referred to as a ventricular diastole or a slowed inflow phase. The period with less cardiac movement refers to a period which has less change in left ventricle volume (a period in which the chart of the left ventricle volume is flat) as shown in FIG. 5. By collecting data during this period, image degradation caused by cardiac movement can be suppressed.

As shown in FIG. 5, a pre-pulse irradiation is performed during the period until which the delay time Td lapses. For instance, the pre-pulse is an inversion pulse, a T2 weighting preparation pulse, a magnetization transfer contrast (MTC) pulse, a dummy shot, a fat suppression pulse, or a pulse to detect respiratory movement. The inversion pulse is a pulse to improve the contrast of an image in the case of, such as, coronary artery imaging or myocardial delayed enhancement. The T2 weighting preparation pulse is a pulse to T2 weighting. The MTC pulse is a pulse to improve contrast using two or more spin-system magnetization transfer. The dummy shot is a pulse to encourage a nuclear spin to achieve a steady state. The fat suppression pulse is a pulse to suppress a fat signal.

A length of a period of low cardiac pulsation is known to change depending on, for instance, the heart rate of a subject. Accordingly, in order to improve image quality, it is preferred that an appropriate delay time Td and window time Tw are set for each subject. A method to support the setting of an appropriate delay time Td and window time Tw for each subject is proposed in (Plein, S. et al, "Three-Dimensional Coronary MR Angiography Performed with Subject-Specific Cardiac Acquisition Window and Motion-adopted Respiratory Gating," AJR; 180:505-512, 2003). In this method, an operator can visually determine the period of low cardiac pulsation by, for instance, performing brief cineradiography, which indicates cardiac movement.

The number of collectable data lines N within one heartbeat can be obtained from a repeating time TR of a pulse sequence and the window time Tw in the following equation.

$N=Tw/TR$

For example, assuming a case in which three-dimensional data is collected when the number of slices, i.e., the number of slice encodes Kz is 60, and the number of matrix Ky in the phase encode direction is 120, the number of required data lines is obtained by the following equation as 7200 lines.

$Kz \times Ky = 60 \times 120 = 7200$

When the window time Tw having less cardiac movement within one cardiac cycle is 100 msec, if the repeating time TR is 5 msec, the number of data lines N collectable within one heartbeat is obtained by the following equation as 20 lines.

$N=100/5=20$

The heart rate required for collecting all data lines necessary for image reconstruction can be obtained by the following equation as 360 heartbeats.

$7200/20=360$

When counting one heartbeat as one second, data collection will be completed in 360 seconds, i.e., six minutes. However, in general, other than the cardiac movement, it is also necessary to consider the body movement caused by the subject's respiration. Therefore, in many cases, a method of selectively collecting data which is less influenced by body movement caused by respiration is simultaneously used. In such case, the actual required data collecting time is further extended.

Figure 6:
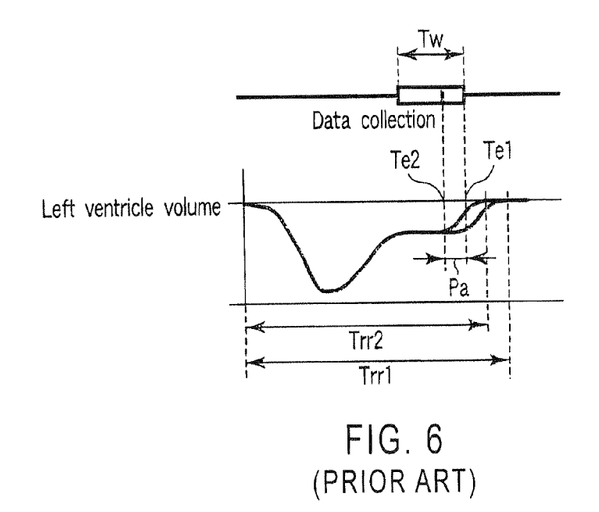
FIG. 6 illustrates an impact of a change in a subject's heart rate on data collection.

The method proposed in Plein is considered to perform effectively in the case where the heart rate of the subject is significantly stable. However, in some cases, the heart rate of the subject may change during the period in which data collection is performed over a long time as mentioned above. If the heart rate rises, duration of a time phase with less cardiac movement becomes shortened, and an appropriate value of the window time Tw also becomes shorter. For example, suppose the window time Tw as shown in FIG. 6 is set in accordance with an R-R interval Trr1 shown in FIG. 6. When the R-R interval is shortened to Trr2 shown in FIG. 6, the point of time where the cardiac movement increases changes from Te1 to Te2. In this case, the heart will move largely during the period of data collection. Further, in the case of FIG. 6, data collected during period Pa will be significantly influenced by cardiac pulsation and will cause a blur in the reconstructed image.

BRIEF SUMMARY

Under such circumstances, imaging has been required to be performed in stable image quality by preventing image degradation caused by change in heart rate.

According to a first aspect of the present invention, there is provided a magnetic resonance imaging apparatus comprising: an acquisition unit to acquire magnetic resonance data in every data group, with regard to magnetic resonance in a subject; a control unit to control the acquisition unit to collect the magnetic resonance data for one or a plurality of data groups during a collection period which is set based on a starting time phase of a cardiac cycle of the subject; a determination unit to determine the magnetic resonance data among the magnetic resonance data acquired by the acquisition unit as ineffective data if at least a part of it is related to a data group acquired during an ineffective period, and as effective data if all of it is related to a data group acquired during a period other than the ineffective period, the ineffective period being set based on an ending time point of the cardiac cycle in which the magnetic resonance data is acquired; and a unit to reconstruct an image regarding the subject by using the effective data.

According to a second aspect of the present invention, there is provided a magnetic resonance imaging apparatus comprising: an acquisition unit to acquire magnetic resonance data in every data line, with regard to magnetic resonance in a subject; a control unit to control the acquisition unit to collect the magnetic resonance data for a plurality of data lines during a collection period which is set based on a starting time phase of a cardiac cycle of the subject; a determination unit to determine the magnetic resonance data among the magnetic resonance data acquired by the acquisition unit as ineffective data if is at least a part of it is related to a data line acquired during an ineffective period, and as effective data if all of it is related to a data line acquired during a period other than the ineffective period, the ineffective period being set based on an ending time point of the cardiac cycle in which the magnetic resonance data is acquired; and a unit to reconstruct an image regarding the subject by using the effective data.

According to a third aspect of the present invention, there is provided a magnetic resonance imaging apparatus comprising: an acquisition unit to acquire magnetic resonance data in every data line with regard to magnetic resonance in a subject; a control unit to control the acquisition unit to collect the magnetic resonance data for one or a plurality of slice encodes during a collection period which is set based on a starting time phase of a cardiac cycle of the subject; a determination unit to determine the magnetic resonance data among the magnetic resonance data acquired by the acquisition unit as ineffective data if at least a part of it is related to a slice encode acquired during an ineffective period, and as effective data if all of it is related to a slice encode acquired during a period other than the ineffective period, the ineffective period being set based on an ending time point of the cardiac cycle in which the magnetic resonance data is acquired; and a unit to reconstruct an image regarding the subject by using the effective data.

According to a fourth aspect of the present invention, there is provided a magnetic resonance imaging method comprising: acquiring magnetic resonance data in every data line with regard to magnetic resonance in a subject; controlling the acquisition to collect magnetic resonance data for a plurality of data lines during a collection period which is set based on a starting time phase of a cardiac cycle of the subject; determining the magnetic resonance data among the acquired magnetic resonance data as ineffective data if it is related to a data line acquired during an ineffective period, and as effective data if it is related to a data line acquired during a period other than the ineffective period, the ineffective period being fixed based on an ending time point of the cardiac cycle in which the magnetic resonance data is acquired; and reconstructing an image regarding the subject by using the effective data.

According to a fifth aspect of the present invention, there is provided a magnetic resonance imaging method comprising: acquiring magnetic resonance data in every data line with regard to magnetic resonance in a subject; controlling the acquisition to collect magnetic resonance data for one or a plurality of slice encodes during a collection period which is set based on a starting time phase of a cardiac cycle of the subject; determining the magnetic resonance data among the acquired magnetic resonance data as ineffective data if at least a part of it is related to a slice encode acquired during an ineffective period, and as effective data if all of it is related to a slice encode acquired during a period other than the ineffective period, the ineffective period being set based on an ending time point of the cardiac cycle in which the magnetic resonance data is acquired; and reconstructing an image regarding the subject by using the effective data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF EXEMPLARY EMBODIMENTS

An exemplary embodiment of the present invention will be explained in reference to the drawings as follows.

Figure 1:
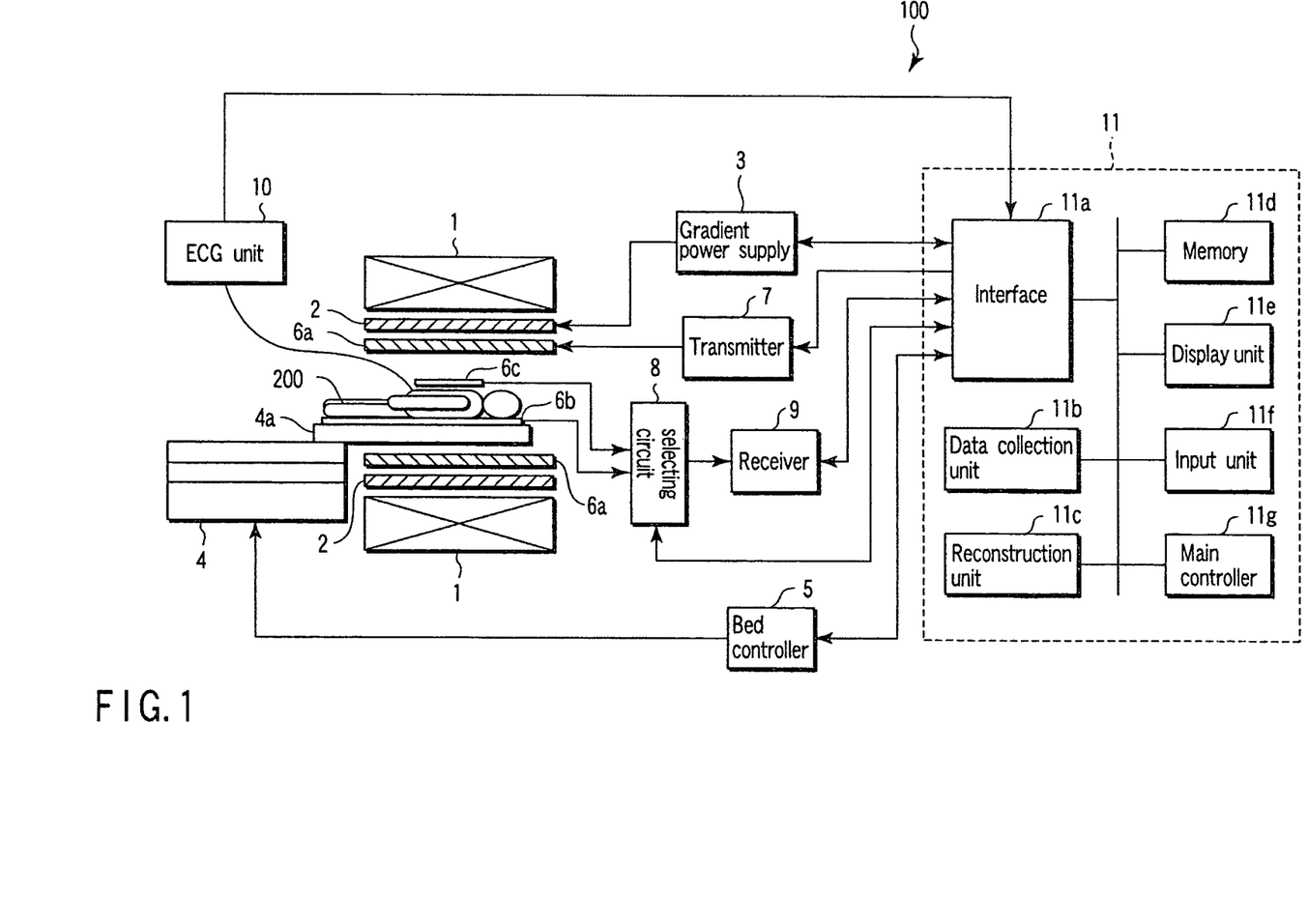
FIG. 1 illustrates a configuration of an MRI apparatus according to an exemplary embodiment of the present invention.

FIG. 1 illustrates a configuration of an MRI apparatus 100 related to the present exemplary embodiment. The MRI apparatus 100 comprises a static field magnet 1, a gradient coil 2, a gradient power supply 3, a bed 4, a bed controller 5, RF coil units 6a, 6b and 6c, a transmitter 7, a selecting circuit 8, a receiver 9, an ECG unit 10 and a computer system 11.

The static field magnet 1 is a hollow cylindrical member, which generates a uniform static magnetic field inside the hollow space. For instance, a permanent magnet or a superconducting magnet is used as the static field magnet 1.

The gradient coil 2 is also a hollow cylindrical member located inside the static field magnet 1. The gradient coil 2 is formed by a combination of three coils corresponding to three axes X, Y and Z which are perpendicular to each other. In the gradient coil 2, the three coils are individually supplied with a current from the gradient power supply 3, thereby generating gradient magnetic fields having their magnetic field intensities varied along the X, Y and Z axes. Assume here that the Z-axis direction corresponds to, for example, the magnetization direction of the static magnetic field. A slice-selecting gradient magnetic field Gs, a phase-encoding gradient magnetic field Ge and a readout gradient magnetic field Gr are formed by combinations of the gradient magnetic fields of each of the X, Y and Z axes. The slice-selecting gradient magnetic field Gs is used to determine an arbitrary imaging section. The phase-encoding gradient magnetic field Ge is used to change the phase of a magnetic resonance signal in accordance with its spatial position. The readout gradient magnetic field Gr is used to change the frequency of a magnetic resonance signal in accordance with its spatial position.

The bed 4 is driven by the bed controller 5 to move its top board 4a in longitudinal (horizontal in FIG. 1) and vertical directions. Normally, the bed 4 is positioned with its longitudinal direction set parallel to the axis of the static field magnet 1. A subject 200 is placed on the top board 4a and, by moving the top board 4a, is inserted into the cavity (imaging space) of the gradient coil 2.

The RF coil unit 6a is made by arranging one or a plurality of coils in a cylindrical case. The RF coil unit 6a is located inside the gradient coil 2, and generates a high frequency magnetic field upon receiving a high frequency pulse (an RF pulse) from the transmitter 7.

The RF coil units 6b and 6c are mounted on the top board 4a, built in the top board 4a, or attached to the subject 200. When imaging is performed, they are inserted into the imaging space along with the subject 200. Array coils are used as RF coil units 6b and 6c. In other words, each of the RF coil units 6b and 6c includes a plurality of element coils. Each of the element coils of RF coil units 6b and 6c receives magnetic resonance signals radiated from the subject 200. Output signals from each element coil are supplied to the selecting circuit 8, individually. The RF coil units for signal reception are not limited to the RF coil units 6b and 6c, and various types of RF coil units may be arbitrarily used for signal reception. In addition, the RF coil units are not limited to two in number. A single RF coil unit may be used; alternatively, three or more RF coil units may be used.

The transmitter 7 transmits an RF pulse signal corresponding to the Larmor frequency to RF coil unit 6a.

The selecting circuit 8 selects signals from among a plurality of magnetic resonance signals output from RF coil units 6b and 6c. The selecting circuit 8 supplies the selected magnetic resonance signals to the receiver 9. The computer system 11 gives instructions to the selecting circuit 8 on which channel to select.

The receiver 9 comprises processing systems corresponding to a plurality of channels, and each processing system includes a preamplifier, a phase detection unit and an analog/digital converter. Magnetic resonance signals selected by the selecting circuit 8 are supplied to these plural-channel processing systems. The preamplifier amplifies magnetic resonance signals. The phase detection unit detects the phase of the magnetic resonance signals output from the preamplifier. The analog/digital converter converts the signals output from the phase detection unit to digital signals. The receiver 9 outputs digital signals produced from each processing system.

The ECG unit 10 includes an ECG sensor which is attached to the surface of the body of the subject 200 to detect an ECG signal as an electric signal. The ECG unit 10 applies various processes including digitalization process to the signal output from this ECG sensor, and outputs such signal to the computer system 11.

The computer system 11 includes an interface 11a, a data collection unit 11b, a reconstruction unit 11c, a memory 11d, a display unit 11e, an input unit 11f and a main controller 11g.

The interface 11a is connected to the gradient power supply 3, bed controller 5, transmitter 7, receiver 9, selecting circuit 8, etc. The interface 11a permits signals to be exchanged between each of these connected units and the computer system 11.

The data collection unit 11b collects digital signals output from the receiver 9. The data collection unit 11b stores the collected digital signals, i.e., magnetic resonance data, in the memory 11d.

The reconstruction unit 11c performs post-processing such as Fourier transform on the magnetic resonance data stored in the memory 11d, thereby acquiring spectrum data or image data corresponding to a desired nuclear spin in the subject 200. Upon ECG gated imaging, the reconstruction unit 11c uses only the magnetic resonance data determined as effective data by the main controller 11g for reconstruction.

The memory 11d stores the magnetic resonance signal data and spectrum data or image data for each subject.

The display unit 11e displays various information items, such as spectrum data or image data, etc., under the control of the main controller 11g. The display unit 11e may be a liquid crystal display, for example.

The input unit 11f receives various instructions or information items input by an operator. The input unit 11f may be a pointing device, such as a mouse or a track ball, a selective device, such as a mode switch, or an input device, such as a keyboard.

The main controller 11g includes a CPU, a memory, etc., and controls the entire MRI apparatus 100 of the present exemplary embodiment. In addition to the functions well known for operating the MRI apparatus 100, the main controller 11g is provided with the following functions. One of its functions is to control the gradient power supply 3, the transmitter 7, the selecting circuit 8, the receiver 9 and the data collection unit 11b, etc., so that the magnetic resonance data for a plurality of data lines can be collected during the collection period which is set based on the starting time phase of the cardiac cycle of the subject 200. One of the above functions is to determine whether the magnetic resonance data is an ineffective data or an effective data based on whether or not it was acquired in an ineffective period. One of the above functions is to control the gradient power supply 3, the transmitter 7, the selecting circuit 8, the receiver 9 and the data collection unit 11b, etc., so that the magnetic resonance data with respect to data lines equivalent to the ineffective data is reacquired.

An operation of the MRI apparatus 100 will be explained.

In the following, it is assumed that a three-dimensional data collection, in which the number of slice encodes Kz is 60 and the number of matrix Ky in the phase encode direction is 120, is performed by an ECG gating in a pulse sequence where the repeating time TR is 5 msec. By collecting data for 20 data lines per cardiac cycle over 360 cardiac cycles based on a window time Tw set as 100 msec, it is assumed that data for a total of 7200 data lines is planned to be collected.

Further, although it may be different from the aspect of the actual cardiac cycle variation, for simplified explanation, a case in which R-R intervals of two continuous cardiac cycles within the 360 cardiac cycles are shorter than the other cardiac cycles is considered.

Figure 2:
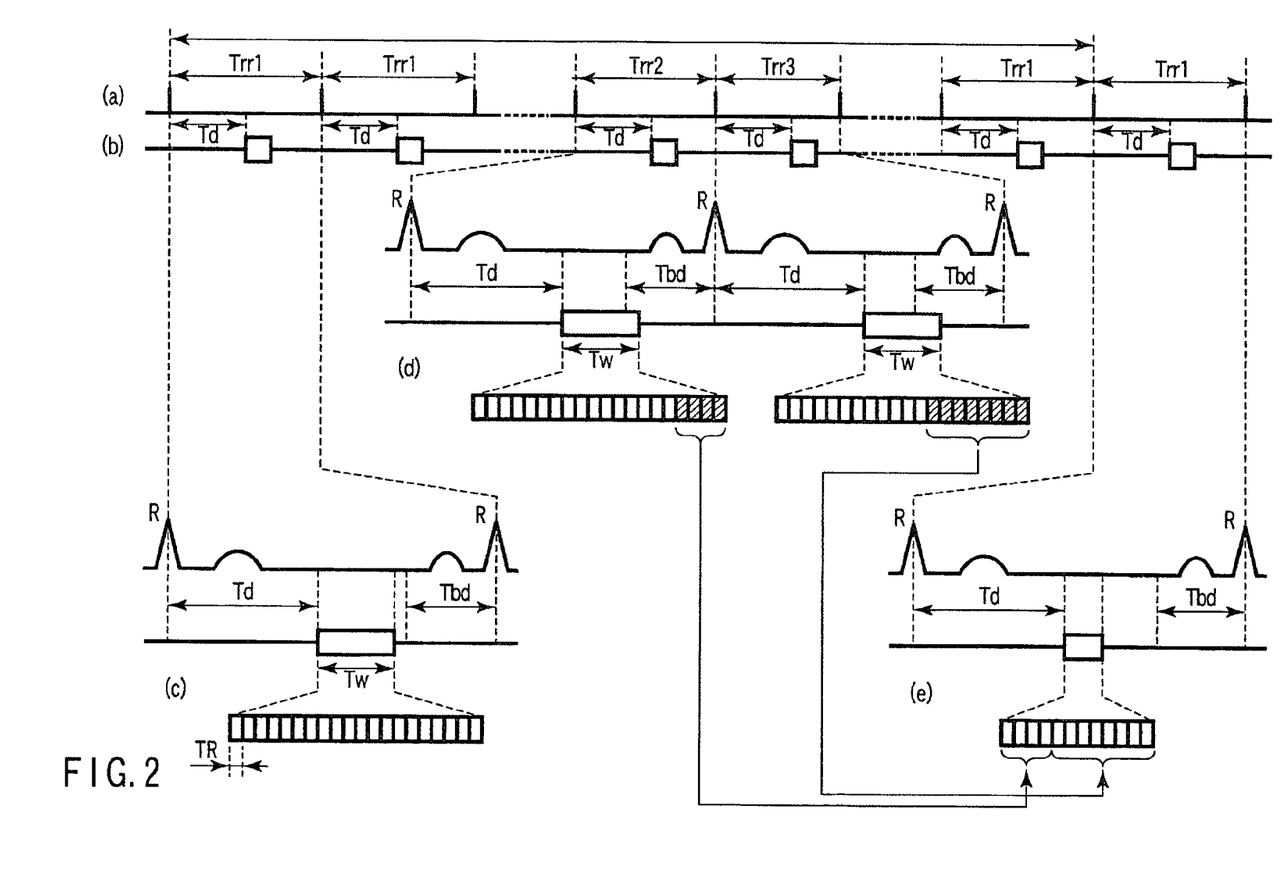
FIG. 2 is a timing diagram showing an example of relation between a subject's ECG waveform and timing to perform data collection.

FIG. 2 is a timing diagram showing an example of a relation between an ECG waveform of a subject 200 and timing of data collection. A part (a) in FIG. 2 shows only a timing of R-wave occurrence in the ECG waveform. Among the 360 cardiac cycles planned for the above data collection, 358 cardiac cycles have an R-R interval of Trr1, and the remaining two cardiac cycles respectively have R-R intervals of Trr2 and Trr3. The relations of these R-R intervals can be described as Trr1>Trr2>Trr3.

A part (b) in FIG. 2 shows a timing of performing data collection. As shown in the part (b), in each cardiac cycle, data is collected for 20 data lines from the lapse of a delay time Td after the occurrence of the R-wave, regardless of the length of the R-R interval in its cardiac cycle. This data collection is performed by, for example, a well-known operation performed by the gradient power supply 3, the transmitter 7, the selecting circuit 8, the receiver 9 and the data collection unit 11b etc., under the control of the main controller 11g.

When the next R-wave occurs on the ECG waveform, the main controller 11g starts a timekeeper of the delay time Td to determine the timing to start collecting data in the cardiac cycle initiated therefrom. At the same time, the main controller 11g determines whether the magnetic resonance data collected in the cardiac cycle which has ended by the R-wave is effective or ineffective.

Meanwhile, in the case where a heart rate of the subject 200 changes, it is known that usually the R-T interval (contraction phase) does not change much, but the T-R interval (expansion phase) stretches (refer to "MDCT and MRI for cardiovascular disease", edited by Sachio Kuribayashi, Hajime Sakuma, Igaku-Shoin, September, 2005, page 16). Accordingly, in the case where the heart rate increases, a portion of the end of the preset data collection window overlaps an atrium diastole, where the cardiac movement is large. In some extreme cases, it crosses over to the next cardiac cycle. The magnetic resonance data collected in a period which crosses the atrium diastole or the border of the cardiac cycle in this manner is significantly affected by cardiac pulsation. Therefore, in the present exemplary embodiment, the ineffective period within a cardiac cycle is set as a period from a predetermined time (hereinafter referred to as backward delay) Tbd prior to a time point of the last R-wave occurrence in the cardiac cycle to a time point of the last R-wave occurrence in the cardiac cycle. The magnetic resonance data with regard to a data line collected even partially in this ineffective period is regarded as ineffective data. Further, the magnetic resonance data with regard to an entire data line collected outside the ineffective period is regarded as effective data.

In order to determine the above, the main controller 11g measures the R-R interval Trr between the newly occurred R-wave and previous R-wave, and determines whether or not Td+Tw is shorter than Trr−Tbd. In the case where Td+Tw is shorter than Trr−Tbd, all magnetic resonance data collected in its cardiac cycle is obtained outside the ineffective period, i.e., within a period with less cardiac movement. Therefore the main controller 11g determines the data as effective data.

A part (c) in FIG. 2 shows details of an ECG waveform, timing for performing data collection and collected magnetic resonance data in a cardiac cycle where the R-R interval is Trr1. In this cardiac cycle, Td+Tw is shorter than Trr1−Tbd. Therefore, magnetic resonance data for 20 lines collected in this cardiac cycle are all regarded as effective data.

Meanwhile, in the case where Td+Tw exceeds Trr−Tbd due to a shortened Trr caused by the increase in heart rate during image taking, at least a part of the magnetic resonance data will be obtained during the atrium diastole where the cardiac movement is large. Accordingly, the magnetic resonance data with regard to the data lines, which even partially are collected during the ineffective period, is regarded as ineffective data, and the magnetic resonance data with regard to the other data lines is regarded as effective data. An nth ($1 \leq n \leq 20$) data line acquired in each cardiac cycle is regarded to be acquired at approximately Td+n·TR time from the previous R-wave. Accordingly, in the case where Td+n·TR<Trr−Tbd is satisfied, the magnetic resonance data regarding the nth acquired data line is regarded as effective data. In the case where the above relation is not satisfied, the magnetic resonance data regarding the nth acquired data line is regarded as ineffective data. Further, the line number or the phase encode amount of the ineffective data line is recorded as uncollected data line information.

A part (d) in FIG. 2 shows details of an ECG waveform, timing for performing data collection and collected magnetic resonance data in a cardiac cycle where the R-R intervals are Trr2 and Trr3. In the cardiac cycle in which the R-R interval is Trr2, Td+Tw is shorter than Trr2−Tbd. In the cardiac cycle in which the R-R interval is Trr3, Td+Tw is shorter than Trr3−Tbd. Further, for the cardiac cycle in which the R-R interval is Trr2, the magnetic resonance data for four data lines shown in a hatch pattern in FIG. 2, and for the cardiac cycle in which the R-R interval is Trr3, the magnetic resonance data for eight data lines shown in a hatch pattern in FIG. 2 are respectively regarded as ineffective data. Furthermore, the magnetic resonance data acquired in the data lines shown without hatch patterns is respectively regarded as effective data.

The effective data is stored in the memory 11d. The ineffective data may be stored separately from the effective data, or may be nullified at this point.

The data lines with regard to these ineffective data will be referred to as uncollected data lines hereinafter. The uncollected data lines can be collected while continuously synchronizing with the ECG waveform after the planned data collection (for example, collecting magnetic resonance data for each of the data lines of the number of phase encodes×the number of slice encodes) is completed.

Specifically, even if ineffective data occurs, data is collected as originally planned during the 360 cardiac cycles. In other words, data required for all 7200 data lines is collected as usual. After ending the original procedure, the main controller 11g confirms whether or not a line number or phase encode amount of the uncollected data line is recorded. If this is recorded, the main controller 11g starts reacquiring the magnetic resonance data regarding the relevant data line.

Reacquisition for each of the uncollected data lines for which the line number or phase encode amount is recorded is performed likewise by the usual data collection mentioned above. If the number of uncollected data lines is 21 or more, the main controller 11g plans recollection by allocating 20 data lines for one cardiac cycle. In the example of FIG. 2, since there are 12 uncollected data lines in total, they are planned to be collected in one cardiac cycle as shown in a part (e) in FIG. 2, and collected. The data acquired in this recollection is also determined as effective or ineffective by the main controller 11g in a similar way as explained above. The recollection is repeated until there is no magnetic resonance data being determined as ineffective data.

If there is no magnetic resonance data that is determined as ineffective data, there will be effective data for all 7200 data lines in the memory 11d. The reconstruction unit 11c reconstructs an image using the effective data.

In this manner, according to the present exemplary embodiment, an image can be reconstructed using only the magnetic resonance data acquired during the period with less cardiac movement even if the heart rate of a subject undergoes changes. Therefore, imaging can be performed in stable image quality without being affected by the cardiac movement.

Meanwhile, in order to reduce the influence from the cardiac movement unfailingly, generally, the window time Tw is set so that there is a sufficient time margin after the data collection and until the increase of cardiac movement. That is to say that, conventionally, data has been collected using only a part of a period having less cardiac movement. Therefore, there has been fewer number of data lines per cardiac cycle, which has caused its imaging time to be extended. In contrast, according to the present embodiment, the number of data lines per cardiac cycle can be improved during a period with less heart rate by setting the window time Tw longer than it has conventionally been set, without considering the above margin. Therefore, the imaging time can be shortened. Moreover, in anticipation of the reduction in the heart rate, imaging time can be further shortened by setting the window time Tw to a value larger than the time width of a period having less cardiac movement at the time of setting. In other words, by setting the data collection window longer than a period which has been confirmed to have less cardiac movement at the time prior to imaging, a larger number of data lines are preplanned to be collected within one cardiac cycle. In this manner, in the case where the heart rate of the subject 200 becomes longer than that measured before imaging, the n satisfying Td+n·TR>Trr−Tbd becomes larger. Therefore, it is possible to collect more data than the number of data lines assumed to be collectable in the period confirmed to have less cardiac movement at the time prior to imaging. If there are more cases in which the heart rate of the subject 200 is long, it would be possible to increase the number of data collected correspondingly, which enables shortening the total imaging time for collecting the entire data.

In the meantime, a prepulse irradiation is performed as shown in FIG. 5 prior to data collection in each cardiac cycle. According to the present exemplary embodiment, since the delay time Td remains constant regardless of the R-R interval, the prepulse irradiation may be preformed at a constant timing on the basis of the R-wave.

The present exemplary embodiment can be exercised in various modifications as follows.

Figure 3:
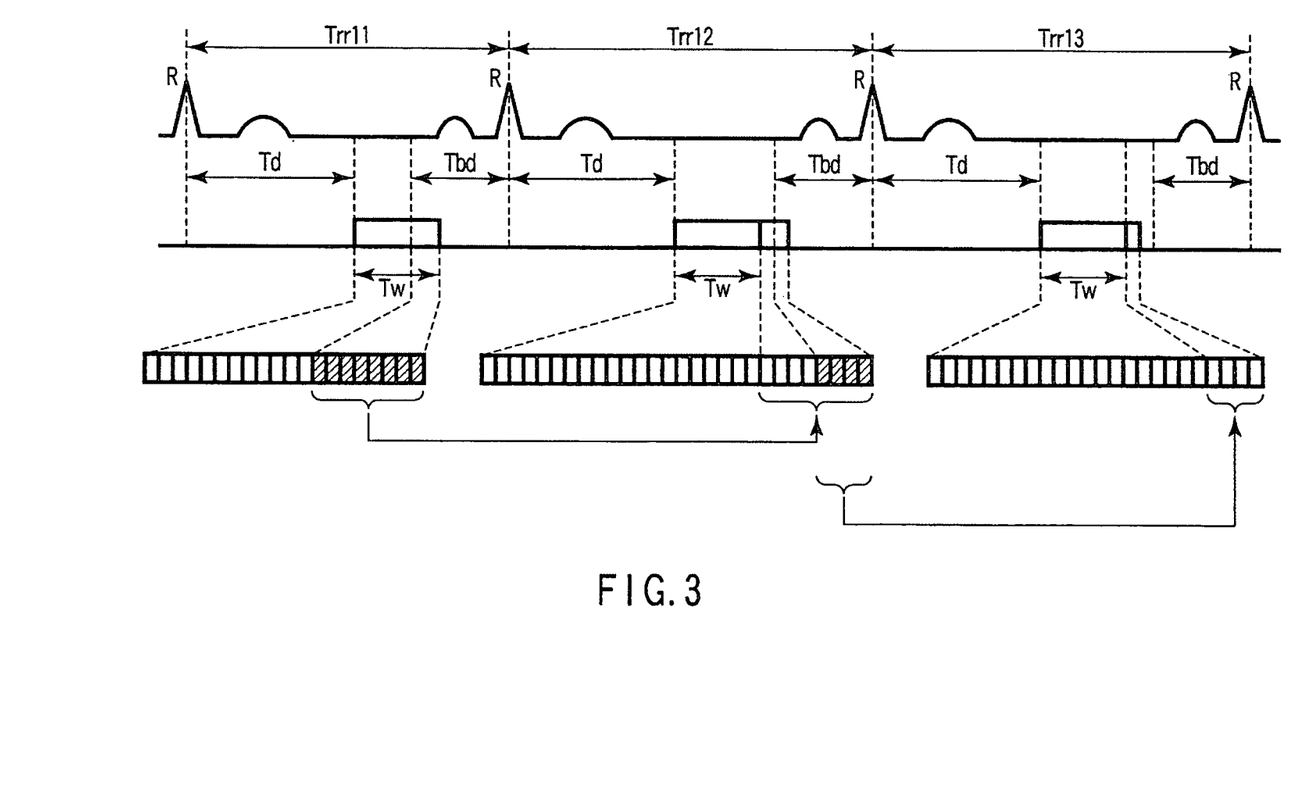
FIG. 3 illustrates a characteristic of a data collecting procedure in a modified exemplary embodiment of the present invention.

The magnetic resonance data regarding the uncollected data lines can be recollected by determining the timing dynamically during imaging. That is, the uncollected data line recorded in a certain cardiac cycle can be planned to be collected after the data line collection planned in the cardiac cycles thereafter has ended. In other words, in the case where the heart rate decreases and the R-R interval Trr is extended in the subsequent cardiac cycles, it is possible to collect the magnetic resonance data of the uncollected data lines after the originally planned data line collection has ended in the instant cardiac cycle. FIG. 3 shows the characteristics of the procedure of the present modified data collection. In FIG. 3, eight lines of uncollected data lines have occurred in the first cardiac cycle. These uncollected data lines are planned to be recollected after collecting data for the originally planned data lines in the next cardiac cycle. In the example of FIG. 3, although four lines of uncollected data lines are successfully recollected by extending the R-R interval from Trr11 to Trr12, the collection of the four other lines of uncollected data lines still remains invalid. In FIG. 3, such four lines which remain uncollected are planned to be recollected after collecting data for data lines originally planned to be collected in the third cardiac cycle. In the example of FIG. 3, since the R-R interval of Trr13 is sufficiently large, the four lines of uncollected data lines are successfully recollected. In this manner, uncollected data lines can be recollected while collecting data for the originally planned data lines. Further, in the case where a succession of heart rate increases causes uncollected data lines to increase, there may be a case in which these uncollected data lines cannot be recollected in one cardiac cycle. In such case, the number of lines attempted to be recollected in one cardiac cycle can be limited to the numbers fixed in advance, and recollection can be planned to be divided over a plurality of cardiac cycles.

If the uncollected data line is a data line adjacent to the end of a k-space, i.e. a data line corresponding to a high space frequency, the magnetic resonance data of the said data line does not contribute to an image contrast. Therefore, it is also fine not to have the magnetic resonance data of such data line recollected. In this case, such data line is filled with 0 data and reconstructed. The range of data lines to be recollected may be fixed, or may be arbitrary set in accordance with the operator's assignment. The range of data line to be recollected may be assigned preferably by spatial frequency or phase encode amounts. Further, by planning data acquirement so that data of data lines from those closest to the k-space center is acquired at an earlier timing of each cardiac cycle, the probability of an uncollected data line becoming a data line adjacent to the end of k-space increases. Therefore, data can be collected efficiently in a condition where the number of uncollected data lines is reduced. In the case where data lines unimportant for reconstruction of the image to be obtained are other than the data lines adjacent to the end of the k-space, it is also fine to exclude such data lines from the recollection target.

The image may also be reconstructed by recollecting neighboring data lines in addition to the uncollected data lines, and using each magnetic resonance data with regard to the neighboring data lines whose data are obtained for the second time. In this manner, an S/N of the reconstruction image can be improved.

The backward delay Tbd can be set by multiplying the R-R interval of each cardiac cycle by a predetermined coefficient of less than 1. In this case, the backward delay Tbd changes for each cardiac cycle.

It is also fine to display an ECG waveform measured by the ECG unit 10 on a setting screen where the operator sets the delay time Td, window time Tw, or the backward delay Tbd, so that assignment of each time can be accepted in accordance with this ECG waveform.

A data group in which the magnetic resonance data is determined as ineffective or not may be arbitrary and does not have to be limited to one data line. For example, in the case of employing a multi-echo method, such as a fast spin echo method, as a pulse sequence, the magnetic resonance data for one slice encode needs to be collected within one cardiac cycle. Further, in the case of two-dimensional imaging, it is desirable that the magnetic resonance data for one slice is collected within one cardiac cycle in order to reduce artifact. Due to such circumstances, in some cases, imaging may be planned to collect magnetic resonance data for one or a plurality of slice encodes within one cardiac cycle. In this case, a data group is regarded as magnetic resonance data for one slice encode.

Figure 4:
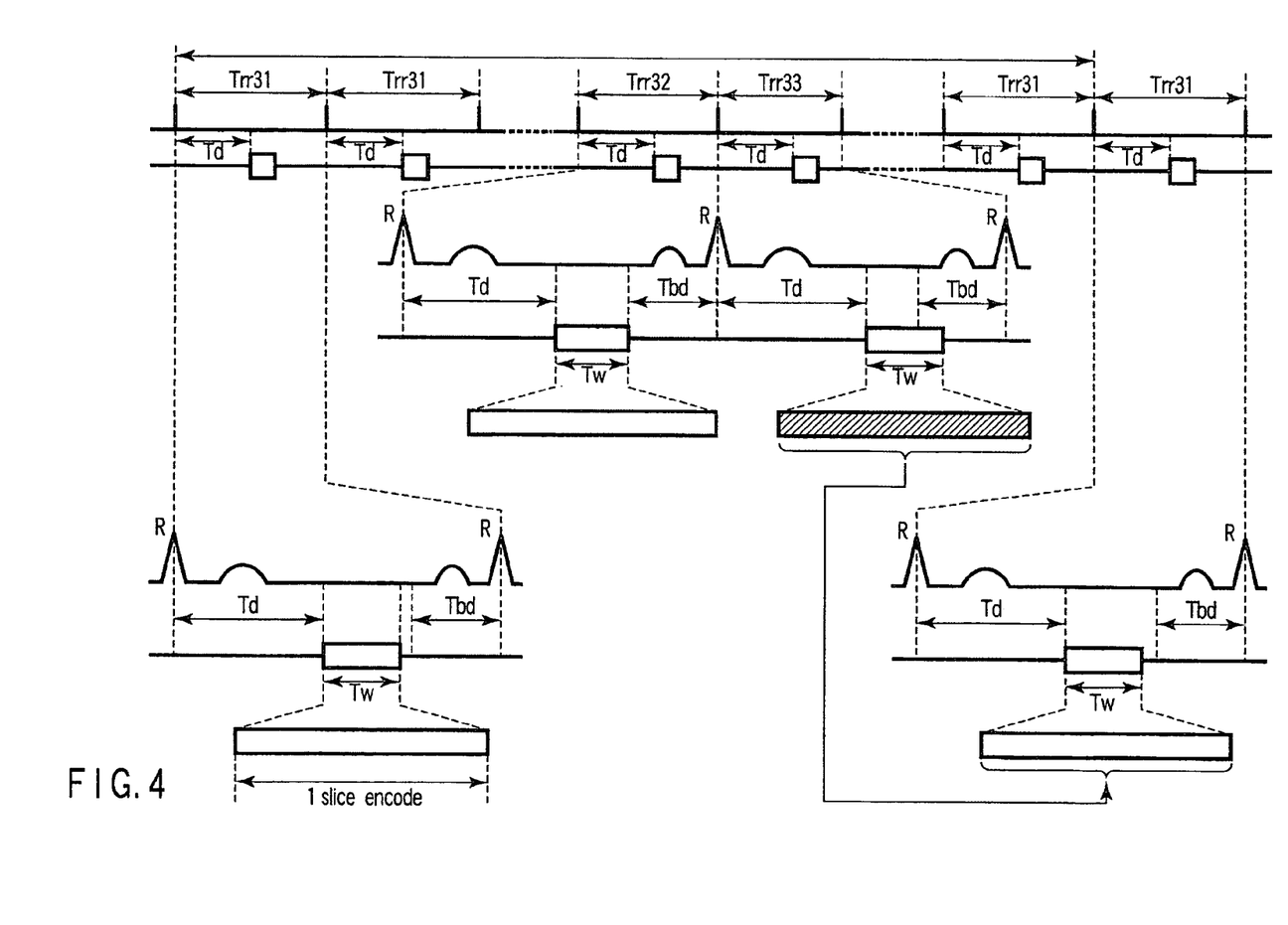
FIG. 4 is a timing diagram showing an example of relation between an ECG waveform and timing to perform data collection in the case of collecting magnetic resonance data for one slice encode in a window time Tw.

FIG. 4 is a timing diagram showing an example of relation between an ECG waveform and timing for executing data collection in the case of collecting magnetic resonance data for one slice encode in a window time Tw. FIG. 4 shows the case of collecting data for Kz slice encodes by collecting one slice encode per cardiac cycle over Kz cardiac cycles. Only two cardiac cycles among the Kz cardiac cycles are Trr32 and Trr33, which have different R-R intervals from the other cardiac cycles Trr31. The relation of these R-R intervals is Trr31>Trr32>Trr33.

In FIG. 4, Td+Tw is shorter than Trr31−Tbd or Trr32−Tbd. Accordingly, the magnetic resonance data of all slice encodes collected in these cardiac cycles is regarded as effective data. However, since Td+Tw is longer than Trr33−Tbd, the magnetic resonance data of all slice encodes collected in this cardiac cycle is regarded as ineffective data. Therefore, the slice encodes regarded as ineffective data are recollected altogether for one slice encode after ending data collection for Kz slice encodes as originally planned.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging (MRI) apparatus comprising:
   static and gradient magnetic field generators, at least one radio frequency (RF) coil coupled to an imaging volume, RF transmitter circuits, RF receiver circuits and a computer stem connected to control said gradient field generator and RF circuits, said computer system being configured to
   acquire MRI data from a subject in plural data groups of k-space;
   collect MRI data for one or a plurality of data groups during a predetermined collection window period which begins at a time point in a cardiac cycle of the subject and continues for a consistent and constant delay time regardless of the length of the cardiac cycle;
   determine acquired MRI data as ineffective data if at least a part of a respectively corresponding data group was acquired during an ineffective period, and as effective data if all of it is acquired during a period other than the ineffective period, the ineffective period being a period prior to an ending time point of the cardiac cycle during which at least part of an atrium diastole occurs to the ending time point of the cardiac cycle;
   record information related to data groups of the ineffective period;
   reacquire effective MRI data related to the data groups specified by the recorded information; and
   reconstruct an image for the subject by using the effective MRI data.

2. The magnetic resonance imaging apparatus according to claim 1, wherein the later occurring predetermined phase of the cardiac cycle is a time phase in which an R-wave occurs in an electrocardiographic waveform of the subject.

3. The magnetic resonance imaging apparatus according to claim 1, wherein the ineffective period is a time period obtained by multiplying the cardiac cycle period by a predetermined coefficient.

4. A magnetic resonance imaging (MRI) apparatus comprising:
   static and gradient magnetic field generators, at least one radio frequency (RF) coil coupled to an imaging volume, RF transmitter circuits, RF receiver circuits and a computer system connected to control said gradient field generator and RF circuits, said computer system being configured to
   acquire MRI data from a subject in plural data lines of k-space;
   collect the MRI data for a plurality of data lines in k-space during a predetermined data acquisition collection window period which begins at a time point in a cardiac cycle of the subject and continues for a consistent and constant data acquisition collection window time regardless of the length of the cardiac cycle;
   determine the acquired MRI data as ineffective data if at least a part of a respectively corresponding data line is acquired during an ineffective period, and as effective data if all of it is related to a data line acquired during a period other than the ineffective period, the ineffective period being a period prior to an ending time point of the cardiac cycle during which at least part of an atrium diastole occurs to the ending time point of the cardiac cycle;
   record information related to data lines of the ineffective period;
   reacquire effective MRI data related to the data lines specified by the recorded information; and
   reconstruct an image for the subject by using the effective MRI data.

5. The magnetic resonance imaging apparatus according to claim 4, wherein MRI data is collected for required data lines, in accordance with a predetermined plan, and MRI data is reacquired for data lines corresponding to the ineffective data after completing an initial collection of MRI data for the entire predetermined plan.

6. The magnetic resonance imaging apparatus according to claim 4, wherein MRI data is collected for required data lines, in accordance with a predetermined plan for each cardiac cycle, and, MRI data is reacquired for data lines corresponding to the ineffective data after completing an initial collection for each cardiac cycle in said predetermined plan.

7. The magnetic resonance imaging apparatus according to claim 4, wherein, if ineffective data is a data line having a low level of importance, reacquisition of MRI data is not acquired for this particular data line.

8. A magnetic resonance imaging (MRI) apparatus comprising:
   static and gradient magnetic field generators, at least one radio frequency (RF) coil coupled to an imaging volume, RF transmitter circuits, RF receiver circuits and a computer system connected to control said gradient field generator and RF circuits, said computer system being configured to
   acquire MRI data from a subject in plural data lines of k-space;
   collect MRI data for one or a plurality of slice encodes during a collection window period which begins at a time point in a cardiac cycle of the subject and continues for a consistent and constant delay time regardless of the length of the cardiac cycle;
   determine acquired MRI data as ineffective data if at least a part of it is from a slice encode acquired during an ineffective period, and as effective data if all of it is from a slice encode acquired during a period other than the ineffective period, the ineffective period being a period prior to an ending time point in the cardiac cycle during which at least part of an atrium diastole occurs to the ending time point of the cardiac cycle;

record information related to slice encodes of the ineffective period;

reacquire effective MRI data related to the data slice encodes specified by the recorded information; and reconstruct an image for the subject by using the effective MRI data.

9. The magnetic resonance imaging apparatus according to claim 8, wherein the later occurring predetermined phase of the cardiac cycle is a time phase in which an R-wave occurs in an electrocardiographic waveform of the subject.

10. The magnetic resonance imaging apparatus according to claim 8, wherein the ineffective period is a time period obtained by multiplying the cardiac cycle period by a predetermined coefficient.

11. The magnetic resonance imaging apparatus according to claim 8, wherein MRI data is collected for required data lines, in accordance with a predetermined plan, and, at the same time MRI data is not reacquired for data lines corresponding to the ineffective data after completing an initial collection of MRI data for the entire predetermined plan.

12. The magnetic resonance imaging apparatus according to claim 8, wherein MRI data is collected for required data lines, in accordance with a predetermined plan for each of a predetermined number of cardiac cycles, and, at the same time MRI data is reacquired for data lines corresponding to the ineffective data after completing an initial collection for each cardiac cycle in said predetermined number.

13. The magnetic resonance imaging apparatus according to claim 8, wherein, if ineffective data is a data line having a low level of importance, collection of MRI data for this particular data line is not resumed.

14. A magnetic resonance imaging (MRI) method comprising:

using an MRI apparatus to acquire MRI data from a subject for plural data lines in k-space;

control the acquisition to collect MRI data for a plurality of data lines in k-space during a predetermined collection window period which begins at a time point in a cardiac cycle of the subject and continues for a consistent and constant delay time regardless of the length of the cardiac cycle;

determine acquired MRI data as ineffective data if it is for a data line acquired during an ineffective period, and as effective data if it is for a data line acquired during a period other than the ineffective period, the ineffective period being a period prior to an ending time point of the cardiac cycle during which at least part of an atrium diastole occurs to the ending time point of the cardiac cycle;

record information related to data lines of the ineffective data;

reacquire effective MRI data related to the data lines specified by the recorded information; and reconstruct an image for the subject by using the effective data.

15. A magnetic resonance imaging (MRI) method comprising: using an MRI apparatus to acquire MRI data from a subject for plural data lines in k-space;

control the acquisition to collect MRI data for one or a plurality of slice encodes during a collection window period which is determined based on a time point in a cardiac cycle of the subject and continues for a consistent and constant delay time regardless of the length of the cardiac cycle;

determine acquired MRI data as ineffective data if at least a part of it is from a slice encode acquired during an ineffective period, and as effective data if all of it is from a slice encode acquired during a period other than the ineffective period, the ineffective period being a period prior to an ending time point of the cardiac cycle during which at least part of an atrium diastole occurs to the ending time point of the cardiac cycle;

record information related to slice encodes of the ineffective data;

reacquire effective MRI data related to the slice encodes specified by the recorded information; and reconstruct an image for the subject by using the effective data.

* * * * *